(12) United States Patent
Phillips

(10) Patent No.: US 10,539,380 B2
(45) Date of Patent: Jan. 21, 2020

(54) METHOD AND SYSTEM FOR THERMOGRAPHIC ANALYSIS

(71) Applicant: HS Marston Aerospace Limited, Wolverhampton, Staffordshire (GB)

(72) Inventor: Paul Phillips, Bromsgrove (GB)

(73) Assignee: HS MARSTON AEROSPACE LIMITED, Staffordshire (GB)

( * ) Notice: Subject to any disclaimer, the term of this patent is extended or adjusted under 35 U.S.C. 154(b) by 0 days.

(21) Appl. No.: 15/473,961

(22) Filed: Mar. 30, 2017

(65) Prior Publication Data

US 2017/0336156 A1   Nov. 23, 2017

(30) Foreign Application Priority Data

May 19, 2016 (GB) .................... 1608817.1

(51) Int. Cl.
| | | |
|---|---|---|
| *G01K 11/00* | (2006.01) | |
| *F28F 27/00* | (2006.01) | |
| *F28G 7/00* | (2006.01) | |
| *G01J 5/50* | (2006.01) | |
| *G01J 5/52* | (2006.01) | |
| *G01N 25/72* | (2006.01) | |
| *G01J 5/00* | (2006.01) | |

(52) U.S. Cl.
CPC .............. *F28F 27/00* (2013.01); *F28G 7/00* (2013.01); *G01J 5/505* (2013.01); *G01J 5/52* (2013.01); *G01N 25/72* (2013.01); *G01J 2005/0081* (2013.01)

(58) Field of Classification Search
CPC combination set(s) only.
See application file for complete search history.

(56) References Cited

U.S. PATENT DOCUMENTS

| | | | |
|---|---|---|---|
| 3,614,889 A | 10/1971 | Gearing | |
| 6,575,620 B1 * | 6/2003 | Banaszak | G01N 3/068 374/4 |
| 6,606,115 B1 | 8/2003 | Alicandro et al. | |
| 6,866,089 B2 | 3/2005 | Avila | |
| 6,931,352 B2 | 8/2005 | Cryer et al. | |
| 7,033,837 B1 * | 4/2006 | Maier | B01J 19/0046 422/68.1 |
| 7,428,919 B2 | 9/2008 | Young et al. | |
| 7,716,987 B2 * | 5/2010 | Sathish | G01N 25/72 250/341.1 |

(Continued)

FOREIGN PATENT DOCUMENTS

| | | |
|---|---|---|
| DE | 102013008004 A1 | 11/2014 |
| EP | 1517138 A1 | 3/2005 |
| JP | 2015125113 A | 7/2015 |

OTHER PUBLICATIONS

UK Search Report for International Application No. GB1608817.1 dated Oct. 27, 2016, 6 pages.

*Primary Examiner* — Lisa M Caputo
*Assistant Examiner* — Nasir U. Ahmed
(74) *Attorney, Agent, or Firm* — Cantor Colburn LLP

(57) ABSTRACT

A method for thermographic analysis of a heat exchanger comprises: applying vibrations to the heat exchanger as a part of a vibration testing process; capturing a thermographic image of at least a portion of the heat exchanger whilst the heat exchanger is undergoing vibrations; analysing the thermographic image; and determining a status of the heat exchanger based on the analysis of the image.

10 Claims, 2 Drawing Sheets

(56) References Cited

U.S. PATENT DOCUMENTS

| | | |
|---|---|---|
| 2004/0051035 A1 | 3/2004 | Zombo et al. |
| 2009/0000382 A1 | 1/2009 | Sathish et al. |
| 2009/0143761 A1* | 6/2009 | Cantor .................. A61N 1/044 604/501 |
| 2010/0019153 A1 | 1/2010 | Zalameda et al. |
| 2011/0062339 A1 | 3/2011 | Ruhge et al. |
| 2011/0106221 A1* | 5/2011 | Neal, II .................. C12N 13/00 607/74 |
| 2011/0295427 A1* | 12/2011 | Motzer .................... B25J 9/162 700/258 |
| 2012/0235579 A1* | 9/2012 | Chemel ................... F21S 2/005 315/152 |
| 2012/0288049 A1 | 11/2012 | Renshaw et al. |
| 2013/0037198 A1* | 2/2013 | Safai ....................... B29C 73/10 156/64 |

\* cited by examiner

METHOD AND SYSTEM FOR THERMOGRAPHIC ANALYSIS

FOREIGN PRIORITY

This application claims priority to United Kingdom Patent Application No. 1608817.1 filed May 19, 2016, the entire contents of which is incorporated herein by reference.

BACKGROUND

The disclosure relates to a method and system for conducting thermographic analysis of a heat exchanger.

Methods of thermography are used for thermographic testing or thermographic analysis of heat exchangers. Typically, thermography includes a stage of inducing a heat flow into a part that is to be inspected, then a step of measuring the infrared signature radiating from the surface of the heat exchanger. This measurement is carried out using a thermal imaging camera and a thermal image of the heat exchanger is generated. The thermal image is then used to help in assessing the working condition of the heat exchanger, and/or in locating any faults or defects in it. For example, if a heat exchanger is heated by flowing hot air through it and has a crack which is venting hot air to the environment, a thermal image of the heat exchanger may help in locating the crack because the hot air would be visible in the thermographic image.

Standard thermographic analysis can therefore indicate whether the status, operational, or safety requirements of a heat exchanger have or have not been met i.e. whether a fault is present in the heat exchanger or not. Little information may be provided on whether any damage has occurred within the heat exchanger, and more importantly on how the nature of such damage developed and changed throughout the life of the heat exchanger.

Typically, thermographic analysis of a heat exchanger is carried out manually by visual inspection of the thermographic image by an expert using judgement to determine whether a defect is present or not.

SUMMARY

Viewed from a first aspect, a method for thermographic analysis of a heat exchanger is disclosed. The method included: applying vibrations to the heat exchanger as a part of a vibration testing process; capturing a thermographic image of at least a portion of the heat exchanger whilst the heat exchanger is undergoing vibrations; analysing the thermographic image; and determining a status of the heat exchanger based on the analysis of the image.

Heat exchangers are subject to mechanical degradation over their operational life. In order to ensure that operational and/or safety requirements are met, the heat exchanger may undergo vibration testing. The vibration testing process may be a type of accelerated life testing that aims to reproduce the effects of vibrations during operational life of the heat exchanger. By capturing thermographic images during vibration testing it is possible to identify heat generated by the vibrations. Heat can be generated due to deformation of the heat exchanger and/or due to friction, for example friction between different parts and/or friction occurring at a crack or other defect. Using thermographic imaging during vibration testing provides a way to identify parts of the heat exchanger that could be redesigned to improve vibration resistance, and/or a way to identify defects as they occur and track defects during the vibration testing process in order to determine how the defect develops. The heat exchanger may be tested until it fails, with the thermographic imaging enabling analysis of the mechanism that lead to the failure.

A vibration test rig may be used in order to determine how the heat exchanger will withstand vibrations that are expected to occur during use of the heat exchanger. The method may include using a vibration testing rig comprising a source of vibrations and a support for holding the heat exchanger and for applying vibrations to the heat exchanger. The vibration test rig may include a mount for mounting a thermal image capturing device for monitoring the heat exchanger during testing.

The heat exchanger may be any suitable type of heat exchanger, particularly any type of fluid/fluid heat exchanger. For example, the heat exchanger may be a gas/gas heat exchanger, a gas/liquid heat exchanger, or a liquid/liquid heat exchanger. In some heat exchanger applications air may be used as the gas. The method may be used for cross flow heat exchangers. Moreover, the heat exchanger may be a heat exchanger that has been manufactured (e.g. from metal) using an additive layer manufacturing technique. Such heat exchangers may have increasingly complex interior topologies and geometries by virtue of the flexibility of the additive manufacturing technique. The disclosed method may allow the defects of such complex heat exchangers to be carefully monitored, modelled and predicted.

One or more accelerometers may be used to measure the vibrations applied to the heat exchanger, for example to determine the frequency of the vibration. The method may include keeping a record of the vibrations along with the thermographic imaging data, to thereby enable the status of the heat exchanger to be linked with the vibrations that are being applied. This can advantageously allow for the formation of defects and/or the degradation of the heat exchanger to be tracked and to be linked with the nature of the vibrations that are being applied. In this way the method can be used to aid in the simulation and design of heat exchangers and the way in which they are used. The method may include identifying potentially problematic vibrations (e.g. certain frequencies) that should be avoided and/or identifying areas of the heat exchanger for redesign in order to reduce the risk of failure and/or to prolong the working life of the heat exchanger.

During the testing of the heat exchanger, capturing a thermographic image of the heat exchanger may include monitoring it using a suitable thermographic sensing device or thermal imaging device such as an infrared thermal imaging camera or the like. The monitoring and measuring of the thermal output of the heat exchanger may be continuous, or may be carried out at intervals. The thermal imaging camera may be installed in-situ with the heat exchanger being tested, and may be positioned facing towards the heat exchanger so as to capture an image of at least a portion of the heat exchanger. The camera may be positioned so as to observe a particular portion or region of the heat exchanger, or may be positioned so as to capture the entire heat exchanger within its field of view. The thermal imaging camera may be located at any suitable position facing the heat exchanger.

As the heat exchanger is exposed to vibrations and heat is generated then the temperature variations within the heat exchanger will cause a change in the infrared radiation radiating away from the heat exchanger, for example differences in intensity and/or wavelength of the radiation. The thermal imaging camera may detect such radiation and provide a real-time thermographic image or thermogram of the heat exchanger which may be used to describe the heat exchanger's current state, and/or to predict the heat exchanger's future state.

The distribution of the infrared radiation from the heat exchanger depends upon its design. For example, differences in materials and structure may affect the thermal output of the heat exchanger. These factors may in turn affect the level of defects or degradation that the heat exchanger experiences.

The vibration testing process may give rise to fractures, cracks or other defects. Such defects may affect the generation of heat from vibration of the heat exchanger and hence change the thermographic image, for example by producing hot spots and/or heat distribution patterns uncharacteristic of an undamaged heat exchanger and hence indicative of a flaw. In this manner, it is possible to obtain important information about how the heat exchanger will behave in response to vibrations. Moreover, information relating to the development and evolution of defects with the heat exchanger may be obtained, such as when the defect first started to occur, at what rate it developed, how long it took to impact the operation of the heat exchanger and so on. In this way, nascent defects may be observed and categorised.

The heat exchanger may be monitored by multiple thermal imaging devices or cameras, with images from the multiple devices being captured and analysed as described above. One camera may be positioned to observe regions of particular interest of the heat exchanger, and one may be positioned to observe the behaviour of the heat exchanger as whole in order to correlate observed changes. Multiple cameras may be positioned facing each major surface of the heat exchanger so as to obtain a complete view or complete thermal map. Cameras may be positioned stereoscopically and hence enable a three-dimensional model of the heat exchanger to be constructed.

Thermographic images may be collected with a particular frequency of capturing the images, and they may be collected automatically or manually. The thermographic camera may be suitable for recording video, as well as for capturing still images. Images may be captured at a predetermined rate. For example, the camera may record images at a frequency of about 60 Hz or about 30 Hz (i.e. video). The camera may record images at a frequency of about 1 Hz, about 0.1 Hz, or about 0.01 Hz, or any other frequency commensurate with the rate of evolution of the thermal signature of the heat exchanger.

Propagation of heat within and through a heat exchanger may directly affect the temporal behaviour of its surface temperature. Moreover, heat distribution will be affected by the interior and exterior geometry and topology of the heat exchanger, as well as its constituent materials. Therefore, a thermographic image or map of the surface temperature may provide information relating to heat flow within the heat exchanger. This may be used for heat exchangers such as a heat exchanger in which the flow of heat is of primary importance.

Analysis of the thermographic image may include determination of any abnormal heat patterns. These may arise as a result of areas of mechanical stress/deformation, cracks, defects, delamination and so on. The analysis may be carried out automatically and may comprise a pre-processing phase for image enhancement and/or noise removal of the thermograms. It may also include a segmentation phase in which regions of interest are identified and extracted.

The thermograms may be analysed using known statistical methods suitable for e.g. determining statistically significant deviations from an expected norm of the image, and may be used for determining whether abnormalities, defects or nascent defects are present in the thermogram. Statistical features may be identified from any regions of interest and may then be classified using an appropriate classification method or combination of methods. Analysed features may include any discrepancy or anomaly compared to the expected heat distribution for the heat exchanger.

The fields of statistical analysis, pattern recognition, and image processing contain a number of established mathematical techniques that may be used for analysis of the captured images. For example, principle component analysis (PCA), neural networks, and/or fuzzy logic may be used. The output of the statistical analysis may be a classification of the feature, and may include an assessment regarding the level or degree of severity of the abnormality in an identified region of interest. It may also include a classification of the type of defect, and/or an estimate of how the defect will evolve. Any suitable combination of methods may be used for analysis of the thermographic image.

The data and images collected throughout a test of a heat exchanger may be gathered, stored and correlated, then associated with a particular defect that occurs in the heat exchanger as a result of the test. Such data may relate to specific heat exchangers, or may have general application to heat exchangers of a particular type. For example, a heat pattern such as a particular hot spot in a heat exchanger may be the consequence of a particular defect e.g. a crack in a particular place in the heat exchanger. By analysing the data and images that give rise to the defect, such defects may be anticipated based on early signs of the occurrence of such a heat pattern. In this manner, early warning signs of defects may be discovered, and hence it is possible to determine that a particular heat exchanger could develop a given fault within an estimable timescale. Discovery of nascent defects is therefore possible, by comparison of observed images with reference images.

To this end, a library or database of defects may be developed and stored, and used as a reference for assessing heat exchangers during analysis. The database may include information about the location of a heat pattern with respect to the heat exchanger, the size of the feature, its shape, intensity, and rate of development over time. The database may further correlate and associate this information with one or more of a particular related defect or type of defect, the vibrations applied, or the heat exchanger or type of heat exchanger to which it relates. Accelerated life testing and in-service testing of heat exchangers may continuously add data to the database, thereby expanding and building upon the library of known defects, and incrementally improving the accuracy of statistical models. This continuous improvement of the database is then increasingly useful for further testing and analysis of heat exchangers. With sufficient data, increasingly accurate assessments of a heat exchanger's status are possible.

A thermographic image, or a part of an image, of all of or a portion of a heat exchanger may therefore be compared against a library of images to assess whether or not any defects are present, and/or whether or not any nascent defects are present which may give rise to further issues. An estimate of the timescale for such issues to occur may also be determined. Comparisons may be made between different images as a whole, or between features selected from images as needed. The comparison may be incorporated into the statistical analysis stage, such that similarities and/or correspondences may be determined using the statistical methods described earlier. A thermal feature which has similar characteristics to those of a defect in the library may indicate the occurrence of such a defect in the heat exchanger.

Therefore, a library may be compiled with sufficient historical data (e.g. during accelerated life testing) and inspection of a heat exchanger and classification of thermal anomalies may be automated. Further analysis data may be gathered during in-service testing, and may be used to refine, update and improve the library. The library may allow the automation and detection of defects in the early stage—nascent defects—that would otherwise not be possible, by associating early thermographic evidence of defects with the final resulting defect.

Some defects which might occur in a heat exchanger may be characterised not only by their thermal features at a single point in time, but by how those thermal features evolve over time. The method may therefore include capturing a second thermographic image of the heat exchanger at a later time, analysing the second thermographic image by any of the disclosed methods, and determining an updated status of the heat exchanger based on the analysis of the second thermographic image, as well as on the analysis of the analysis of the first image and the determined status of the heat exchanger. The updated status may be a confirmation of the first determined status, or may be the determination of a different status indicating e.g. a different defect. In this way, multiple thermal images may be captured and used to increase the accuracy and certainty of detection of a defect in the heat exchanger. A third thermographic image and optionally then further thermographic images may be captured and used in the same process as for the second thermographic images referenced above.

Active thermography offers different inspection methods as well as a variety of measurement techniques, so that the measurement procedure may be optimally adapted to different materials, parts, and/or heat exchangers with different structural properties.

Thermographic analysis may be used as part of a Non-Destructive Testing (NDT) process for heat exchangers, as it can provide information relating the rates of material degradation and can aid in identifying root causes of in-service failures. It can also be used to verify thermal models and simulations of heat exchanger wear and degradation. It can allow detailed information on the rate of degradation to be measured and stored for future reference e.g. in a library.

Viewed from a second aspect a system for thermographic analysis of a heat exchanger is disclosed. The system includes: a source of vibrations for applying vibrations to the heat exchanger as a part of a vibration testing process; an imaging device for capturing a thermographic image of at least a portion of the heat exchanger whilst the heat exchanger is undergoing vibrations; and a data processor for analysing the thermographic image and for determining a status of the heat exchanger based on the thermographic image.

The system may include a vibration test rig, such as a test rig arranged to determine how the heat exchanger will withstand vibrations that are expected to occur during use of the heat exchanger. The vibration testing rig may comprise the source of vibrations and a support for holding the heat exchanger and for applying vibrations to the heat exchanger. The vibration test rig may include a mount for mounting a thermal image capturing device for monitoring the heat exchanger during testing.

The system may include one or more accelerometer(s) for measuring the vibrations applied to the heat exchanger, for example to determine the frequency of the vibration. The data processor may receive data from the accelerometer(s) and may keep a record of the vibrations along with the thermographic imaging data, to thereby enable the status of the heat exchanger to be linked with the vibrations that are being applied.

The system may be arranged to perform thermographic analysis as discussed above in relation to the first aspect and the optional features thereof, for example including apparatus features as mentioned above having functions as described above.

The imaging device may include an output for outputting the thermographic image to the data processor. The output of the image may be automatic. The imaging device may be arranged to view the whole heat exchanger, or may be arranged to view a portion or preferred region of the heat exchanger. The system may comprise a plurality of imaging devices for capturing thermographic images of at least a portion of the heat exchanger. The imaging devices may be arranged to view the heat exchanger from opposing positions, or complementary positions. The imaging devices may be arranged stereoscopically so at to provide images that may be used to construct a three-dimensional image of the heat exchanger.

The data processor may be configured to perform any or all image analysis steps discussed above. Thus, during analysis of the received thermographic image the data processor may identify preferred regions of the image, or regions of interest. These regions may correspond to regions of the heat exchanger that are of particular interest, are prone to developing defects, and/or are critical to safe or efficient operation of the heat exchanger. These regions may be regions containing thermal anomalies. The data processor may be arranged to reduce noise in the image, to reduce the file size of the image, to enhance the image, and/or to filter the image with a predetermined image filter.

The data processor may segment the image into predetermined regions, or segment the image into dynamically determined regions. The data processor may be arranged to identify thermal anomalies or features, and to extract characteristics of those features from the image, and/or to use the extracted characteristics to inform the segmentation of the image.

The system may further comprise a database which stores a library of defects. The library may comprise information about the location of a thermal feature with respect to the heat exchanger, the size of the feature, its shape, intensity, and/or rate of development over time. The library may correlate and associate this information with a particular defect or type of defect, the historical data regarding the defect, its evolution over time, and/or the heat exchanger or type of heat exchanger to which it relates. The library may be configured to be updated (e.g. by the data processor controlling the database) so that the library is updated based on the information extracted from the thermographic images in combination with a defect which occurs in the heat exchanger. The database could be located within the same computer system as the data processor, or it may be remotely located, for example accessible via a computer network.

The data processor may access and read the database and compare characteristics of thermal features of the images to information stored in the database, and may use that information to determine the status of the heat exchanger and the nature of any defects or nascent defects visible in the thermographic image.

The system may include a display for displaying the thermographic image, and/or for displaying the results of the analysis of the image and the determination of the status of the heat exchanger.

The data processor may be configured to control the system. The data processor may be configured to carry out any and all of the method steps described earlier.

Viewed from another aspect a computer program product comprising instructions for execution on a system for thermographic analysis of a heat exchanger is disclosed. The system includes a source of vibrations for applying vibrations to the heat exchanger as a part of a vibration testing process; an imaging device for capturing a thermographic image of at least a portion of the heat exchanger whilst the heat exchanger is undergoing vibrations; and a data processor. When executed on the system the instructions will cause the system to: capture a thermographic image of at least a portion of the heat exchanger whilst vibrations are being applied to the heat exchanger, analyse the thermographic image, and determine a status of the heat exchanger based on the analysis of the image.

The analysis may be carried out by the processor. The processor may be caused to control the imaging device. The program may cause the system to apply vibrations via the source of vibrations and to monitor the vibrations using one or more accelerometer(s). The program may cause the system to update a library of defects in a database based on thermographic information.

The program may cause the system or the data processor to carry out any and all of the processes described above in relation to the method and system of the above aspects and the optional features thereof. The system for thermographic analysis for which the computer program product is intended may be a system having features as described above in relation to the second aspect and optional features thereof.

BRIEF DESCRIPTION OF THE DRAWINGS

Preferred embodiments of the invention are described below by way of example only and with reference to the accompanying drawings, in which.

DETAILED DESCRIPTION

Figure 1:
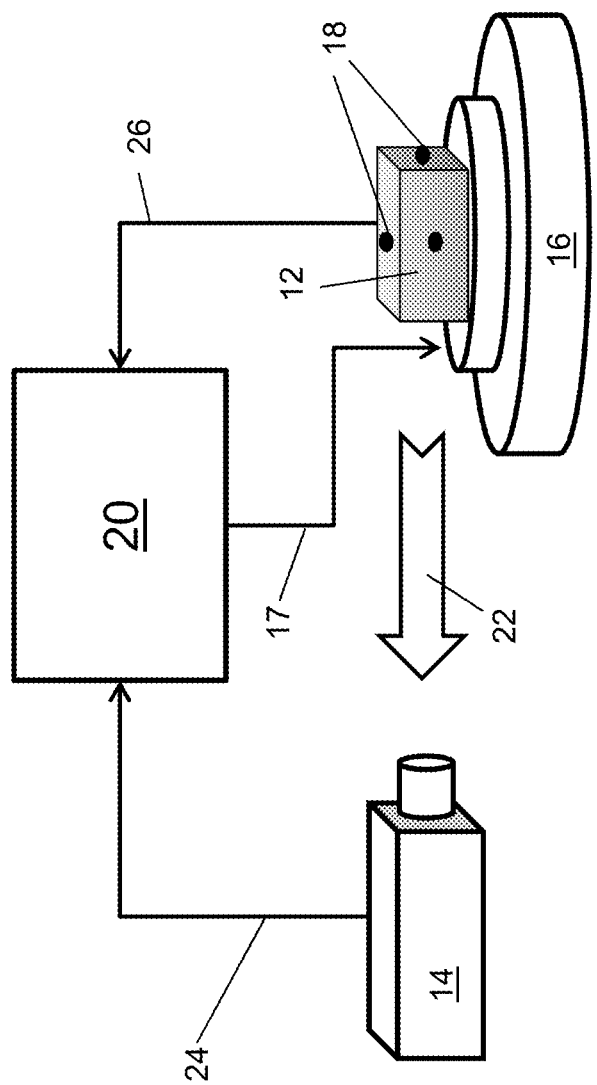
FIG. 1 shows a schematic of a system for thermographic imaging during vibration testing.

A system for conducting thermographic analysis of a heat exchanger 12 during vibration testing is shown in FIG. 1. The system comprises a thermal imaging device 14, and a vibration source in the form of an acceleration test rig 16. These types of test rigs 16 are also referred to as "shakers". The thermal imaging device 14 is an active infrared camera 14 configured to detect radiation in the infrared (IR) range (i.e. between 700 nanometres to 1 millimetre). The camera 14 is directed at the heat exchanger 12 and is positioned so that its field of view encompasses at least a portion of the heat exchanger 12. Accelerometers 18 are attached to the heat exchanger 12 in order to measure the vibrations experienced by the heat exchanger 12 during the testing. A computer system 20 is coupled to the infrared camera 14, the acceleration test rig 16 and the accelerometers 18. The computer system 20 is arranged to act as a control system and a data processing system and hence controls the acceleration test rig 16 by providing an acceleration input 17 instructing it to perform a required acceleration/vibration test, as well as receiving data from the accelerometers 18 and the infrared camera 14.

Figure 2:
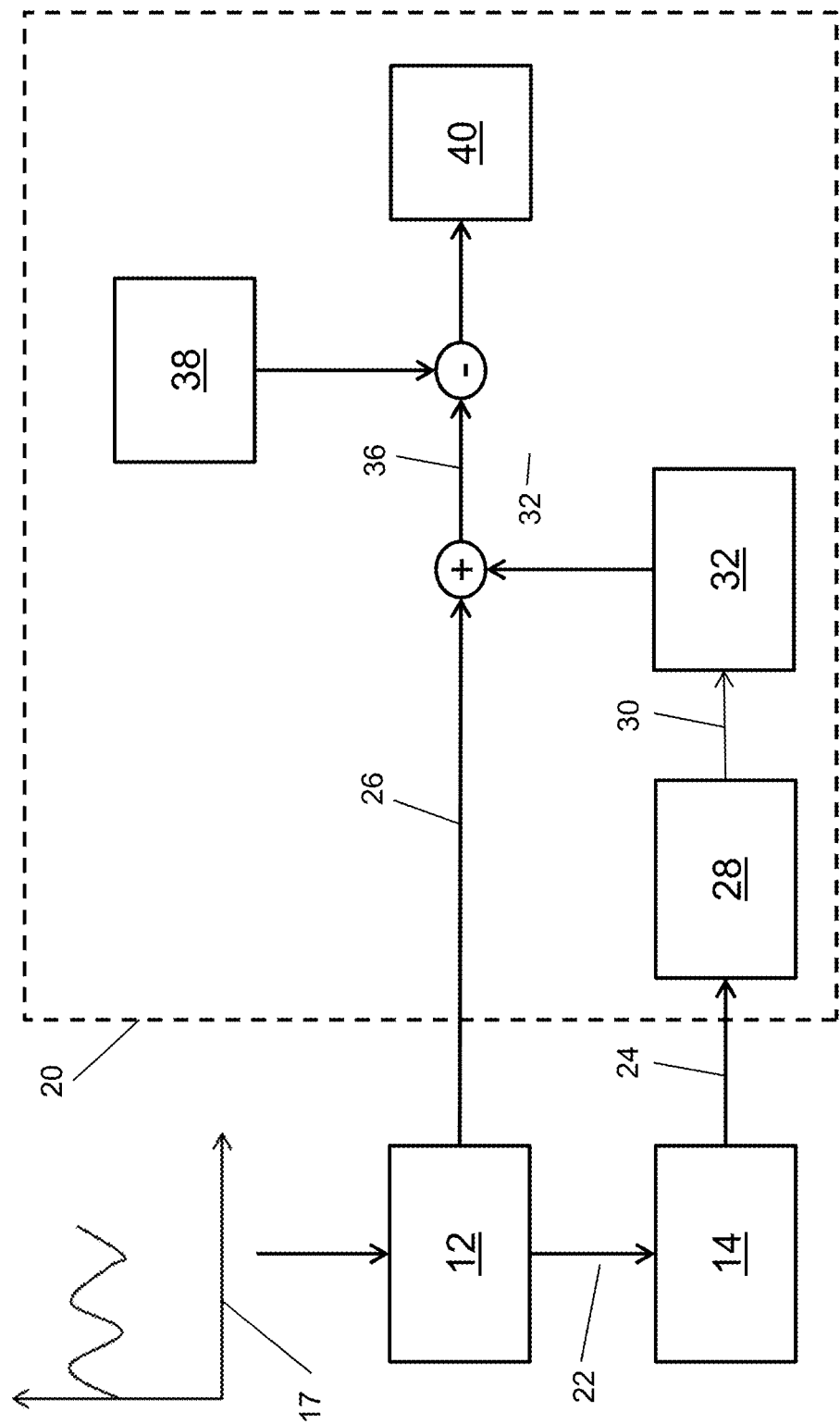
FIG. 2 is a diagram showing analysis of thermographic and vibration data.

During vibration testing of the heat exchanger 12 on the acceleration test rig 16 the heat exchanger 12 emits energy in the form of infrared radiation 22. Some of the energy applied by the acceleration test rig 16 is dissipated as heat, which is generated by mechanical deformation of the heat exchanger 12 and/or friction. As explained above, the pattern of heat generation is affected by the shape and structure of the heat exchanger 12 as well as by the presence of any defects such as cracks and so on. The camera 14 detects the IR radiation 22 and outputs a thermographic image data 24 to a data processor. The data processor forms part of the computer system 20. The computer system 20 also receives output signals 26 from the accelerometers 18. FIG. 2 includes a schematic representation of the data connections 24, 26 to the computer system 20, as well as the various steps that are carried out by the computer system 20 (for example, by the data processor).

The computer system 20 is configured to receive the thermographic image data from the camera 14 and the accelerometer output signals 26 from the accelerometers 18 and to analyse them according to desired methods. The analytical methods may be statistical and mathematical, as described before. The data processor may store the image for future reference, for example in a memory of the computer system 20 and/or may display it on a display of the computer system 20. The computer system 20 also has access to a database for storing a library of defects, i.e. a record of thermal patterns corresponding to known defect types. This database may be on the memory of the computer system 20 or it may be remotely located, i.e. at some other point within a computer network to which the computer system is connected.

When the heat exchanger 12 includes a defect then this affects the distribution and spectrum of the emitted IR radiation 22 during the vibration testing, which hence differs compared to a healthy heat exchanger i.e. a heat exchanger without a defect. For example, in some cases the defect will increase local friction and/or deformation during vibration and hence the IR radiation 22 has a higher intensity than expected in the region near the defect. Other defects may prevent thermal energy concentrating in their proximity by directing it elsewhere in the heat exchanger 12 or by reducing local deformations (for example, by acting as a stress reliever). In that case the IR radiation 22 has a lower intensity than expected. The relationship between the defect and the thermal patterns on the heat exchanger 12 surface can depend on multiple factors, such as for example the internal/external geometry of the heat exchanger 12, its constituent materials, and the characteristics of the vibrations applied by the acceleration test rig 16. For example, different amplitudes and/or different frequencies of vibration will create different responses at the heat exchanger 12.

The data processor is arranged to perform a number of image pre-processing steps. For example, the data processor reduces noise in the image or enhances contrast and/or intensity differences. The data processor then partitions the image into regions of interest using statistical methods, thereby highlighting any e.g. hot spots, cold spot, or other thermal anomalies. For example, the data processor might identify a statistically significant hot spot in a particular region of the heat exchanger.

In the next stage, the data processor isolates the region of interest and the relevant features therein (e.g. hot spots, cold spots, anomalies etc.). The data processor has already been provided with information concerning the type of heat exchanger 12 and hence already has information about what a correctly functioning (i.e. healthy) heat exchanger 12 should look like. The data processor then performs an analysis upon the thermal features to determine relevant characteristics thereof. The characteristics include the location of the region in the image and with relation to the heat exchanger, the shape of the region, and the intensity of the thermal features. The data processor may be supplied with information about the heat exchanger 12 being tested before it receives the raw thermographic image from the camera 14 so as to better assess the presence of anomalies. The data processor may instead check for thermal features within (or outside) predetermined parameters.

The data processor is configured to then compare the determined characteristics to the library of known characteristics stored in the database. This comparison includes the use of statistical methods as described above to compare the features to known characteristics. The data processor then judges the nature of the defect based on the results of the comparison. For example, when the analysis of the image determines a hot spot located in the centre of the heat exchanger 12 of a given intensity and approximately circular distribution, the data processor compares these characteristics to find similar thermal patterns for known defects in the database and then determines the type of the defect.

Having made this determination, the data processor may provide estimates of the evolution of the defect based on the data read from the database. The defect may be of a type that is known to evolve into a critical fault e.g. within several more weeks of use. Alternatively, the defect can be of a sort that will not develop further, or will not significantly affect the operation of the heat exchanger 12.

FIG. 2 also includes the main steps in a method of analysis of the thermographic data 24 and vibration data 26. As already discussed above the acceleration input 17 provided via the acceleration test rig 16 results in vibrations at the heat exchanger 12, which are measured by accelerometers 18 with the resulting output signals 26 being passed to the computer system 20. The thermographic images from the cameras 14 are also passed to the computer system 20 as thermographic image data 24. The computer system 20 includes one or more image processing module(s) 28, which pre-process the image data 24, for example to remove noise and/or enhance the image characteristics. If necessary then the image processing module(s) 28 can process the image data 24 to combine data from multiple images, which might be multiple images from different cameras 14 at different positions and/or multiple images from the same camera at different times. This produces a combined thermal map 30 that is passed to a feature extraction module 32 of the computer system 20. In the feature extraction module 32 the regions of interest of the image are determined, and the thermal features of those regions are extracted from the image and analysed. The features are classified and identified, which can include comparing characteristics of the extracted features to a database of known defect characteristics.

The extracted/identified features together with the combined thermal map 30 together form an enhanced thermal map 34 that is combined with the accelerometer output signals 26 to provide combined thermal and vibration data 36. This is then used together with input from a stress model 38 to allow for wide-ranging further steps, for example correlation of defects with vibration inputs, identification of potential weak areas in the design of the heat exchanger 12, cross-checking of predictions from the stress model 38, identification of areas where the stress model 38 is inaccurate and so on. The final output data 40 can be used for further manual or automated analysis of the heat exchanger 12 and/or the stress model 38. The final output data 40 might include recommendations for further action and/or proposed decisions concerning any of the steps discussed above.

By use of the above described method and system, inspectors and heat exchanger designers can be aided in analysis of in-service failures of heat exchangers. Automatic classification of thermal features removes human error based upon subjective decision making and allows for fully continual monitoring of the image data without the inconsistencies that would arise with continuous monitoring via a human operator. The thermographic analysis coupled with the vibration testing process may be used to help validate and/or improve stress models and simulations of the heat exchanger. Data regarding defects gathered during the vibration testing may be used to compile a library of defects, which may inform analysis of heat exchangers during in-service testing. Further, analysis of heat exchangers during in-service testing can be used to improve and update the library of defects, thereby constantly improving accuracy and usefulness of the system. Thermography analysis according to the present method allows the rate of degradation of a part to be accurately estimated. Further, little training is required for the technology and thermal images and classification results are intuitive.

Although the present disclosure has been described with reference to particular embodiments, the skilled reader will appreciate that modifications may be made that fall within the scope of the disclosure as defined by the appended claims.

The invention claimed is:

1. A method for thermographic analysis of a heat exchanger, the method comprising:
   applying vibrations to the heat exchanger with a source of vibrations as a part of a vibration testing process;
   capturing a thermographic image of at least a portion of the heat exchanger whilst the heat exchanger is undergoing vibrations;
   analysing the thermographic image;
   determining a status of the heat exchanger based on the analysis of the image;
   wherein determining a status of the heat exchanger includes comparing at least one feature of the captured thermographic image with a library of heat exchanger defects to classify the at least one feature of the thermographic image based on that comparison; and
   updating the library of heat exchanger defects based on the captured thermographic image.

2. A method as claimed in claim 1, further comprising:
   measuring with one or more accelerometers the vibrations applied to the heat exchanger; and
   recording the measured vibrations along with the thermographic imaging data, to thereby enable the status of the heat exchanger to be linked with the vibrations that are being applied.

3. A method as claimed in claim 1, further comprising:
   identifying potentially problematic vibrations that should be avoided or identifying areas of the heat exchanger for redesign in order to reduce the risk of failure and/or to prolong the working life of the heat exchanger.

4. A method as claimed in claim 1, wherein analysis of the thermographic image includes identification of a region of interest of the image, wherein the region of interest includes an anomalous thermal feature.

5. A method as claimed in claim 1, wherein analysis of the thermographic image includes determination of at least one characteristic of at least one anomalous thermal feature of the captured thermographic image.

6. A method as claimed in claim 1, wherein the captured thermographic image is a first thermographic image, the method further comprising:
- capturing a second thermographic image of at least a portion of the heat exchanger;
- analysing the second thermographic image; and
- determining an updated status of the heat exchanger based on the analysis of the second thermographic image and the determined status of the heat exchanger based on the analysis of the first image.

7. A system for thermographic analysis of a heat exchanger, the system comprising:
- a source of vibrations for applying vibrations to the heat exchanger as a part of a vibration testing process;
- an imaging device for capturing a thermographic image of at least a portion of the heat exchanger whilst the heat exchanger is undergoing vibrations; and
- a data processor for analysing the thermographic image and for determining a status of the heat exchanger based on the thermographic image, wherein when determining a status of the heat exchanger the data processor compares at least one feature of a captured thermographic image with a library of defects to classify the at least one feature of the captured thermographic image based on that comparison and updating the library based on the captured thermographic image.

8. A system as claimed in claim 7, further comprising:
- a vibration test rig including the source of vibrations and a support for holding the heat exchanger and for applying vibrations to the heat exchanger.

9. A system as claimed in claim 7, further comprising:
- one or more accelerometer(s) for measuring the vibrations applied to the heat exchanger,
- wherein the data processor is arranged to receive data from the accelerometer(s) and record the data, the data representing of the vibrations along with the thermographic imaging data, to thereby enable the status of the heat exchanger to be linked with the vibrations that are being applied.

10. A computer program product comprising instructions stored on a non-transitory medium for execution on a system for thermographic analysis of a heat exchanger, the system comprising a source of vibrations for applying vibrations to the heat exchanger as a part of a vibration testing process; an imaging device for capturing a thermographic image of at least a portion of the heat exchanger whilst the heat exchanger is undergoing vibrations; and a data processor, the instructions, wherein when executed on the system causing the system to:
- capture a thermographic image of at least a portion of the heat exchanger whilst vibrations are being applied to the heat exchanger, analyse the thermographic image;
- determine a status of the heat exchanger based on the analysis of the image, wherein determining a status of the heat exchanger includes comparing at least one feature of the captured thermographic image with a library of heat exchanger defects to classify the at least one feature of the thermographic image based on that comparison; and
- update the library of heat exchanger defects based on the captured thermographic image.

* * * * *